(12) United States Patent
Tanaka et al.

(10) Patent No.: US 11,329,366 B2
(45) Date of Patent: May 10, 2022

(54) WIRELESS COMMUNICATION DEVICE, SENSOR DEVICE, AND WEARABLE DEVICE

(71) Applicants: OMRON Corporation, Kyoto (JP); OMRON HEALTHCARE Co., Ltd., Kyoto (JP)

(72) Inventors: Hirokazu Tanaka, Kyoto (JP); Hiroshi Miura, Kyoto (JP); Shohei Iwata, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 0 days.

(21) Appl. No.: 16/940,596

(22) Filed: Jul. 28, 2020

(65) Prior Publication Data
US 2020/0358168 A1 Nov. 12, 2020

Related U.S. Application Data

(63) Continuation of application No. PCT/JP2019/004249, filed on Feb. 6, 2019.

(30) Foreign Application Priority Data

Feb. 14, 2018 (JP) .............................. JP2018-024413

(51) Int. Cl.
*H01Q 1/27* (2006.01)
*H01Q 1/24* (2006.01)
(Continued)

(52) U.S. Cl.
CPC ............. *H01Q 1/243* (2013.01); *A61B 5/022* (2013.01); *H01Q 1/38* (2013.01); *H01Q 13/10* (2013.01); *H04Q 1/24* (2013.01)

(58) Field of Classification Search
CPC .......... H01Q 1/243; H01Q 1/38; H01Q 13/10; H01Q 1/273; H01Q 1/44; A61B 5/022;
(Continued)

(56) References Cited

U.S. PATENT DOCUMENTS 5,331,608 A 7/1994 Umemoto et al.
9,837,705 B2 12/2017 Aizawa et al.
(Continued)

FOREIGN PATENT DOCUMENTS

CN 1843288 A 10/2006
CN 104570718 A 4/2015
(Continued)

OTHER PUBLICATIONS

Chinese Office Action and Search Report, dated Dec. 17, 2020, for Chinese Application No. 201980008073.6, with English machine translations.
(Continued)

*Primary Examiner* — David E Lotter
(74) *Attorney, Agent, or Firm* — Birch, Stewart, Kolasch & Birch, LLP

(57) ABSTRACT

A wireless communication device comprising: a case having a substantially cylindrical shape and including a first opening at a front surface and a second opening at a back surface, respectively; a first cover member that blocks at least a portion of the first opening;
a second cover member that blocks at least a portion of the second opening; an insulating member that fills a gap between the first cover member and the case; a display; a substrate housed by the case; an antenna circuit installed on the substrate; and a communication circuit installed on the substrate and electrically connected to the antenna circuit, wherein the case includes a metal
(Continued)

material; and the first cover member includes a light-transmitting material that allows light from the display to pass through.

9 Claims, 10 Drawing Sheets

(51) Int. Cl.
*A61B 5/022* (2006.01)
*H01Q 1/38* (2006.01)
*H01Q 13/10* (2006.01)
*H04Q 1/24* (2006.01)

(58) Field of Classification Search
CPC .......... A61B 5/002; A61B 5/681; H04Q 1/24; G04G 9/0064; G04G 21/04; G04G 17/08; G04G 17/04; G04G 21/025; G04G 21/00
See application file for complete search history.

(56) References Cited

U.S. PATENT DOCUMENTS

| | | | |
|---|---|---|---|
| 9,912,044 | B2 | 3/2018 | Iijima et al. |
| 10,218,060 | B2 | 2/2019 | Aizawa et al. |
| 10,424,833 | B2 | 9/2019 | Aizawa et al. |
| 10,485,478 | B1* | 11/2019 | Mirov ................. H02J 7/025 |
| 10,651,547 | B2 | 5/2020 | Aizawa et al. |
| 2007/0030154 | A1 | 2/2007 | Aiki et al. |
| 2009/0003141 | A1 | 1/2009 | Ozawa |
| 2012/0119956 | A1 | 5/2012 | Chen et al. |
| 2014/0206954 | A1* | 7/2014 | Yuen ................. A61B 5/0022 600/301 |
| 2015/0109172 | A1 | 4/2015 | Iijima et al. |
| 2016/0049721 | A1 | 2/2016 | Aizawa et al. |
| 2017/0086743 | A1* | 3/2017 | Bushnell ............ A61B 5/681 |
| 2018/0069304 | A1 | 3/2018 | Aizawa et al. |
| 2018/0090826 | A1 | 3/2018 | Da Costa Bras Lima et al. |
| 2019/0072912 | A1* | 3/2019 | Pandya ............... A61B 5/332 |
| 2019/0165459 | A1 | 5/2019 | Aizawa et al. |
| 2019/0183430 | A1* | 6/2019 | Alphonse ............ A61B 5/742 |
| 2019/0372206 | A1 | 12/2019 | Aizawa et al. |
| 2020/0358167 | A1* | 11/2020 | Tanaka ................. H01Q 1/38 |

FOREIGN PATENT DOCUMENTS

| | | |
|---|---|---|
| CN | 205721108 U | 11/2016 |
| CN | 206878175 U | 1/2018 |
| JP | S53-134478 A | 11/1978 |
| JP | H5-81787 U | 11/1993 |
| JP | 2003-35787 A | 2/2003 |
| JP | 2003-152582 A | 5/2003 |
| JP | 2004-28918 A | 1/2004 |
| JP | 2005-20074 A | 1/2005 |
| JP | 2005-200743 A | 7/2005 |
| JP | 2006-105654 A | 4/2006 |
| JP | 2008-45878 A | 2/2008 |
| JP | 2008-54890 A | 3/2008 |
| JP | 2008-167899 A | 7/2008 |
| JP | 2009-8496 A | 1/2009 |
| JP | 2010-197662 A | 9/2010 |
| JP | 2012-154768 A | 8/2012 |
| JP | 2015-81825 A | 4/2015 |
| JP | 2016-40884 A | 3/2016 |
| JP | 3213686 U | 11/2017 |
| WO | WO 2016/003953 A1 | 1/2016 |

OTHER PUBLICATIONS

English translation of International Preliminary Report on Patentability dated Oct. 15, 2020, in PCT International Application No. PCT/JP2019/004249 (Forms PCT/IB/338 and PCT/ IPEA/409).
International Search Report of the International Searching Authority for PCT/JP2019/004249 dated Mar. 19, 2019.
English translation of International Search Report of the International Searching Authority for PCT/JP2019/004249 dated Mar. 19, 2019.
International Preliminary Report on Patentability Chapter II for PCT/JP2019/004249 dated Jan. 16, 2020.
English translation of International Preliminary Report on Patentability dated Aug. 20, 2020, in PCT International Application No. PCT/JP2019/004249 (Forms PCT/IB/338 and PCT/IPEA/409).
Office Action dated Aug. 10, 2021, in Chinese Patent Application No. 201980008073.6.
Japanese Office Action for Japanese Application No. 2018-024413, dated Dec. 7, 2021, with English translation.

\* cited by examiner

WIRELESS COMMUNICATION DEVICE, SENSOR DEVICE, AND WEARABLE DEVICE

CROSS-REFERENCE TO RELATED APPLICATIONS

This is a continuation of International Application PCT/JP2019/004249, with an international filing date of Feb. 6, 2019, filed by applicant, and of International Application JP 2018-024413, with an international filing date of Feb. 14, 2018, the disclosure of which is hereby incorporated by reference in its entirety.

TECHNICAL FIELD

The present invention relates to an electronic device provided with an antenna.

BACKGROUND ART

In recent years, various wearable devices have entered the market. Wearable devices, also referred to as wearable computers, are portable computers that can be worn by a user.

Wearable devices can be used, for example, for user health management. Further, the wearable device may connect with another computer, such as a smart phone, to exchange information with the other computer. For example, some smart watches include sensors that measure the user's heart rate, blood pressure, and the like and can transmit this biological information to the smart phone.

There is a demand for wearable devices to be compact so that they can be comfortably worn by users, for example. For example, smart watches, a type of wearable device, are expected to have a similar compactness to that of normal wrist watches.

Wearable devices typically connect with other computers via wireless communication and therefore require an antenna. The antenna can be attached on the outside of the wearable device; however, this may result in the antenna being damaged when the wearable device is worn as well as requiring an electrically conductive structure between the antenna and a substrate and waterproofing of this structure. On the other hand, particularly in the case of the case of a wearable device being compact and including a metal material, there are many restrictions on the layout relating to disposing the antenna in the electronic device while maintaining the necessary emission efficiency, such as: antenna space saving, mitigation of electrical interference with another metal component, ensuring an emission port for electromagnetic waves, and the like; thus, disposing an antenna inside a wearable device, in particular one with a metal case, is difficult.

JP 2016-40884 A relates to technology for an antenna space saving arrangement. In this Patent Document, a metal bezel disposed in a case body of an electronic device and a metal ribbon included in an antenna are electromagnetically coupled, and an equivalent electrical length of the ribbon is set to be shorter than the ¼ wavelength.

Also, JP 2003-152582 A relates to technology for mitigating electrical interference between an antenna and another metal component. In this Patent Document, a wrist watch type information device is described in which an IC for wireless communication and a chip antenna are installed so as not to overlap in a plan view to reduce the possibility of electrical interference between the internal devices.

Furthermore, JP 2015-81825 A and JP 2003-35787 A relate to technology for ensuring an emission port for electromagnetic waves. JP 2015-81825 A describes a configuration in which an outer case is made of plastic and an antenna is arranged with a maximum radiation direction thereof intersecting a thickness direction of the outer case and arranged in a position not overlapping a metal bezel in the maximum radiation direction. This configuration prevents a satellite signal from a GPS satellite from being blocked by the bezel. JP 2003-35787 A describes a radio-controlled clock including: a non-metal main lid; and a back lid that includes a metal auxiliary lid, with a slit being formed by cutting a portion of the metal auxiliary lid to allow standard waves to pass through the slit.

SUMMARY OF INVENTION

An objective of the present disclosure is to install an antenna inside an electronic device while minimizing or preventing a reduction in emission efficiency.

According to a first aspect of the present disclosure, a wireless communication device comprises:

a case having a substantially cylindrical shape and including a first opening at a front surface and a second opening at a back surface, respectively;

a first cover member that blocks at least a portion of the first opening;

a second cover member that blocks at least a portion of the second opening;

an insulating member that fills a gap between the first cover member and the case;

a display;

a substrate housed by the case;

an antenna circuit installed on the substrate; and a communication circuit installed on the substrate and electrically connected to the antenna circuit, wherein the case includes a metal material;

the first cover member includes a light-transmitting material that allows light from the display to pass through; and the second cover member does not include a metal material in at least one region of the second cover member.

In the wireless communication device, the insulating member fills the gap between the case and the first cover member, and an electrical slit is formed in the gap. Thus, according to the wireless communication device, an emission port for electromagnetic waves transmitted and received by the antenna circuit can be secured. Moreover, the electrical slit has little limitation on the flexibility of the design of the wireless communication device.

In the wireless communication device according to the first aspect, the case may include a projection portion projecting to an inner side of the first opening and the second opening and provided on an inner wall surface connecting to the first opening and the second opening; and the insulating member may fill a gap between: the projection portion and the inner wall surface; and the first cover member. In this way, the first cover member can be supported by the projection portion on the inner wall of the case and an electrical slit can be formed between the two.

In the wireless communication device according to the first aspect, the second cover member may not include any metal material in at least one region of the second cover member; and a first orthographic projection of the at least one region of the second cover member projected on a plane substantially parallel with the substrate may contain a second orthographic projection of an installed region of the antenna circuit projected on the plane identical. According to the wireless communication device, the antenna circuit and the region of the second cover member not including a metal material overlap in a plan view. Thus, a reduction in the emission efficiency of the antenna circuit due to being disposed inside the housing containing a metal material is minimized or prevented.

According to a second aspect of the present disclosure, a sensor device comprises:

the wireless communication device according to the first aspect; and a sensor that measures a physical quantity and generates sensor data, wherein the communication circuit transmits the sensor data via the antenna circuit.

According to the second aspect, the sensor device including the wireless communication device according to the first aspect can be provided.

According to a third aspect of the present disclosure, a sensor device comprises:

the wireless communication device according to the first aspect; and a sensor that measures a physical quantity and generates sensor data, wherein the display displays the sensor data. According to the third aspect, the sensor device including the wireless communication device according to the first aspect can be provided.

In the sensor device according to the third aspect, the sensor may include a blood pressure monitor. According to the sensor device (hereinafter referred to as the sensor device according to the fourth aspect of the present disclosure), the user's blood pressure can be measured and displayed on the display.

According to a fifth aspect of the present disclosure, a wearable device comprises:

the sensor device according to the fourth aspect; and a belt member connected to the case. The wearable device can measure the user's blood pressure, display the data on a display, and/or transmit the data via the wireless communication device according to the first aspect.

According to a sixth aspect of the present disclosure, a wireless communication device comprises:

a case having a substantially cylindrical shape and including a first opening at a front surface and a second opening at a back surface, respectively;

a first cover member that blocks at least a portion of the first opening;

a support member that supports the first cover member;

a second cover member that blocks at least a portion of the second opening;

an insulating member that fills a gap between the first cover member and the support member;

a display;

a substrate housed by the case; and an antenna circuit installed on the substrate;

a communication circuit installed on the substrate and electrically connected to the antenna circuit, wherein the case includes a metal material;

the first cover member includes a light-transmitting material that allows light from the display to pass through; and the second cover member does not include a metal material in at least one region of the second cover member.

In the wireless communication device, the insulating member fills the gap between the support member and the first cover member, and an electrical slit is formed in the gap. Thus, according to the wireless communication device, an emission port for electromagnetic waves transmitted and received by the antenna circuit can be secured. Moreover, the electrical slit has little limitation on the flexibility of the design of the wireless communication device.

In the wireless communication device according to the sixth aspect, the support member may have a substantially cylindrical shape that includes a third opening at a front surface and a fourth opening at a back surface, respectively, and include a projection portion projecting to an inner side of the third opening and the fourth opening and provided on an inner wall surface connecting to the third opening and the fourth opening; the first cover member may be supported by the projection portion; and the insulating member may fill a gap between: the projection portion and the inner wall surface; and the first cover member. In this way, the first cover member can be supported by the projection portion on the inner wall of the support member, and an electrical slit can be formed between the two.

According to a seventh aspect of the present disclosure, a wireless communication device comprises:

a case having a substantially cylindrical shape and including a first opening at a front surface and a second opening at a back surface, respectively;

a first cover member that blocks at least a portion of the first opening;

a support member that supports the first cover member;

a second cover member that blocks at least a portion of the second opening;

an insulating member that fills a gap between the support member and the case;

a display;

a substrate housed by the case; and an antenna circuit installed on the substrate;

a communication circuit installed on the substrate and electrically connected to the antenna circuit, wherein the case includes a metal material;

the first cover member includes a light-transmitting material that allows light from the display to pass through; and the second cover member does not include a metal material in at least one region of the second cover member.

In the wireless communication device, the insulating member fills the gap between the case and the support member, and an electrical slit is formed in the gap. Thus, according to the wireless communication device, an emission port for electromagnetic waves transmitted and received by the antenna circuit can be secured. Moreover, the electrical slit has little limitation on the flexibility of the design of the wireless communication device.

In the wireless communication device according to the seventh aspect, the case may include a projection portion projecting to an inner side of the first opening and the second opening and provided on an inner wall surface connecting to the first opening and the second opening; the support member may be supported by the projection portion; and the insulating member may fill a gap between: the projection portion and the inner wall surface; and the support member. In this way, the support member can be supported by the projection portion on the inner wall of the case, and an electrical slit can be formed between the two.

According to the present disclosure, an antenna can be installed inside an electronic device while minimizing or preventing a reduction in emission efficiency.

DESCRIPTION OF EMBODIMENTS

An embodiment according to an aspect of the present invention (hereinafter, also referred to as "the present embodiment") will be described below with reference to the drawings.

Note that elements that are the same as or similar to the elements described hereinafter are given the same or similar reference signs, and duplicate descriptions will be omitted.

1 Application Example

Figure 1:
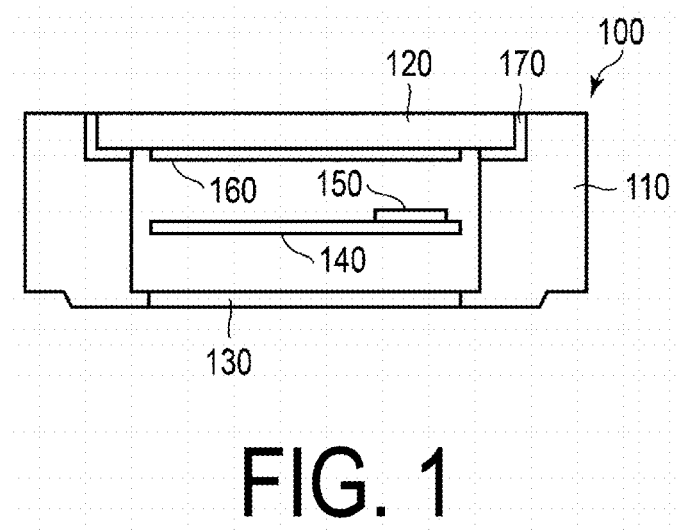
FIG. 1 is a diagram illustrating an application example of an electronic device according to an embodiment.

First, an application example of the present embodiment will be described with reference to FIG. 1. FIG. 1 schematically illustrates an application example of an electronic device according to the present embodiment. An electronic device 100 is, for example, a wearable device, such as a smart watch, that displays, on a display 160, a user's blood pressure measured by a sensor unit not illustrated in FIG. 1 or transmits the user's blood pressure to another computer, such as a smart phone, connected with the electronic device 100. As described below, the electronic device 100 may be referred to as a wireless communication device when considering it is provided with an antenna circuit 150, which is a wireless communication interface (I/F), and a communication circuit not illustrated in FIG. 1 or may be referred to as a sensor device when considering it is provided with a sensor unit not illustrated FIG. 1.

As illustrated in FIG. 1, the electronic device 100 includes a case 110, a glass lid 120, a back lid 130, a substrate 140, an antenna circuit 150, a display 160, and an insulating member 170. FIG. 1 illustrates an example of a cross-section of the electronic device 100 sectioned through the antenna circuit 150 in a plan view substantially perpendicular to the surface of the electronic device 100.

The case 110 has a substantially cylindrical shape with an opening on a front surface and a back surface. The case 110 is made of metal (in other words, is a conductor) or may include a metal material (for example, a metal-plated non-metal material). This increases the durability of the case 110 and gives it a high-class design. Also, as described below with reference to FIG. 7, this also has the effect of artificially extending the electrical length of the antenna circuit 150. The case 110 include a projection portion that is provided on an inner wall surface connecting to the openings and that projects toward the opening inner side. The glass lid 120 is supported by the projection portion of the case 110 with a gap formed therebetween.

The glass lid 120 blocks the opening (or at least a portion thereof) on the front surface side of the case 110. The glass lid 120 includes glass or another light-transmitting material and allows light from the display 160 to pass through itself. That is, the user can view the display content of the display through the glass lid 120. Note that the glass lid 120 may simply be referred to as a cover member.

The back lid 130 blocks the opening (or at least a portion thereof) on the back surface side of the case 110. The back lid 130 may be made of metal but from the perspective of minimizing or preventing a reduction in emission efficiency, preferably does not include any metal material or does not include any metal material in at least one region thereof. The at least one region is, for example, defined as the region overlapping the installed region of the antenna circuit 150 as seen in a plan view. Specifically, an orthographic projection of the region of the back lid 130 not including a metal material projected on a plane substantially parallel with the substrate 140 contains an orthographic projection of the installed region of the antenna circuit 150 projected on the same plane. That is, the back lid 130 (or at least one region thereof) can be used as an emission port for electromagnetic waves transmitted and received by the antenna circuit 150. The back lid 130 may be connected to the case 110 by being screwed together, for example. The back lid 130 may also simply be referred to as a cover member.

The substrate 140 is housed in the case 110, may be provided with the antenna circuit 150 disposed on the substrate 140 as well as the communication circuit described below, and installed with electronic components such as a battery; and metal components. The substrate 140 will be described in detail below.

The antenna circuit 150 is designed to operate with microwaves, for example, electromagnetic waves at or near the 2.4 GHz band used by Bluetooth (trade name), Wi-Fi (trade name) and the like. Here, Bluetooth may include at least Bluetooth Low Energy (BLE), which is the version 4.0 specification. The ¼ wavelength of electromagnetic waves in the 2.4 GHz band is approximately 3 cm, However, as described below, by using the parasitic capacitance that occurs between the antenna circuit 150 (or the antenna element provided therein) and the case of the electronic device 100 as a capacity hat connected to the antenna circuit 150, the electrical length of the antenna circuit 150 can be pushed below the ¼ wavelength of the target frequency. Note that the target frequency of the antenna circuit 150 is not limited to the 2.4 GHz band. The antenna circuit 150 will be described in detail below.

The display 160, for example, is a liquid crystal display, an organic electroluminescence (EL) display, or the like. The display 160 displays video, still images, text, and the like. Specifically, the display 160 may display sensor data generated by a sensor unit not illustrated in FIG. 1, data received from a user device described below, and the like.

The insulating member 170 fills the gap between the projection portion of the case 110 and the glass lid 120. The insulating member 170 seals the gap and increases waterproofing and dustproofing and forms an electrical slit, through which electromagnetic waves can pass, between the internal space and the external space of the case 110. The electrical slit can be used as an emission port for electromagnetic waves transmitted and received by the antenna circuit 150. Note that a gap may be formed between the insulating member 170 and the display 160 as illustrated in FIG. 1, or the insulating member 170 may be in contact with the display 160.

The length of the emission port is preferably equal to or greater than the ¼ wavelength of the target frequency. In the case in which the glass lid has a disk shape with a diameter of approximately 3 cm, an emission port the size of the outer circumference, i.e., approximately 10 cm, can be secured. This is a greater than 3 cm, which is the length of the emission port required by electromagnetic waves in the 2.4 GHz band. The electrical slit is formed utilizing the gap between components of the electronic device 100 and does not require the case 110 or other components to be processed, for example, cut or the like. Thus, there is little limitation on the flexibility of the design of the electronic device 100.

As described above, in the electronic device 100 according to the application example, the insulating member 170 fills the gap between the case 110 and the glass lid 120, and an electrical slit is formed in the gap. Thus, according to the electronic device 100, an emission port for electromagnetic waves transmitted and received by the antenna circuit 150 can be secured. Moreover, the electrical slit has little limitation on the flexibility of the design of the electronic device 100.

2 Configuration Example

Figure 2:
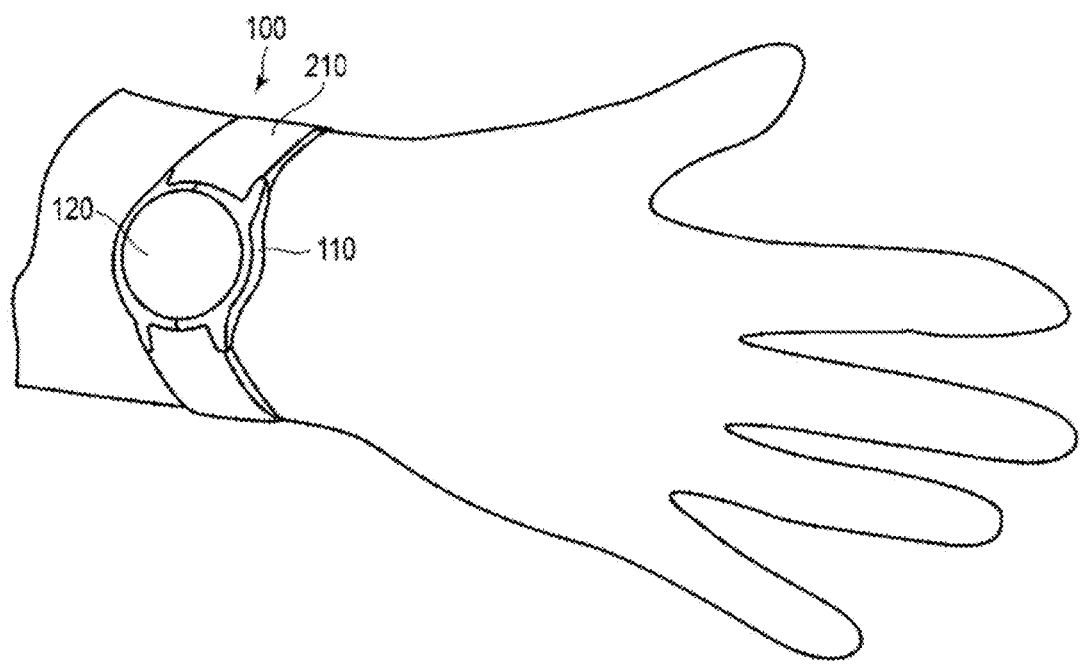
FIG. 2 is a perspective view illustrating an example of an electronic device according to an embodiment.

FIG. 2 illustrates an example of the appearance of the electronic device 100 according to an embodiment. Although the electronic device 100 is shaped similar to a wrist watch like a smart watch in FIG. 2, the shape of the electronic device 100 is not limited thereto. In FIG. 2, a belt member 210 connected to the case 110 is illustrated.

The belt member 210 is connected to the back surface of the case 110, the back lid 130, or another support body. The user can wear the electronic device 100 by wrapping the belt member 210 around the wrist such that the back surface of the case 110 faces inward. Note that, as described below, in the case in which the electronic device 100 includes a blood pressure monitor as one of its sensor units, the belt member 210 may be used as a cuff.

Figure 3:
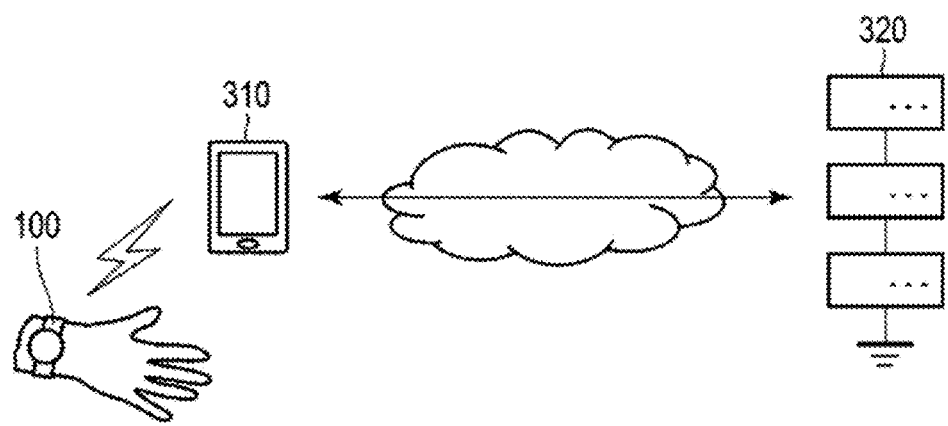
FIG. 3 is a diagram illustrating an example of a system including an electronic device according to an embodiment.

As illustrated in FIG. 3, the electronic device 100 is connected to a user device 310, which is another computer, such as a smart phone, tablet terminal, laptop, and the like. The electronic device 100 and the user device 310 may be connected using near-field wireless communication such as Bluetooth, for example. The electronic device 100 may, as necessary, transmit sensor data, such as blood pressure data, motion data (for example, acceleration data or angular velocity data), and step data calculated based on motion data, activity data, calories burned data, and the like, to the user device 310. Conversely, the electronic device 100 may receive various data, such as incoming notifications, mail notifications, and the like, from the user device 310 and display it on the display.

The user device 310 receives sensor data from the electronic device 100 using Bluetooth, WiFi, or the like. On the other hand, the user device 310 may transmit various data for display on the electronic device 100 to the electronic device 100. Also, the user device 310 may also be connected to a server 320 via a network, as illustrated in FIG. 3. However, the connection between the user device 310 and the server 320 is not required, and the electronic device 100 and the user device 310 may be connected together. The user device 310 transmits sensor data via a network to the server 320 using mobile communications, such as 3G, 4G, and the like; Wi-Fi; Wi-max; and the like.

In addition, the user device 310 may display the sensor data transmitted by electronic device 100 as a graph. The user device 310 may be installed with an application for managing sensor data.

The server 320 accumulates sensor data transmitted from the user device 310. The server 320, for example, may transmit the user's sensor data in response to access from an insurance company or a personal computer (PC) of a program operator as a provision for user's insurance subscription assessments, performance evaluation of health promoting programs, and the like.

Figure 4:
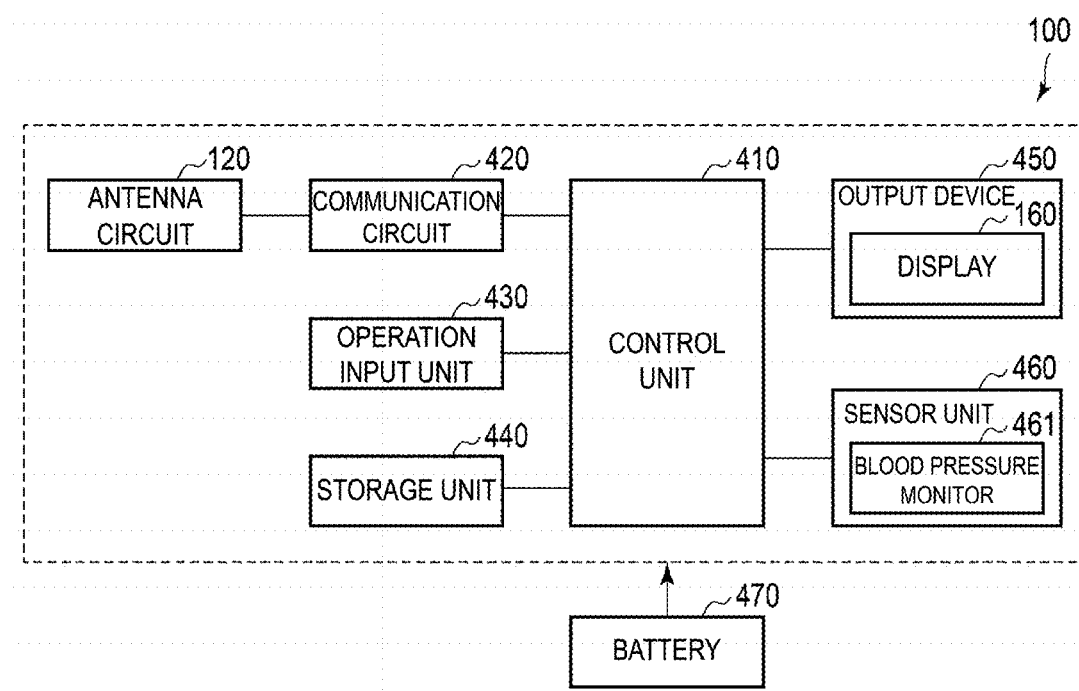
FIG. 4 is a block diagram illustrating an example of the hardware configuration of an electronic device according to an embodiment.

Next, an example of the hardware configuration of the electronic device 100 will be described with reference to FIG. 4. FIG. 4 schematically illustrates an example of the hardware configuration of the electronic device 100.

As illustrated in FIG. 4, the electronic device 100 according to the present embodiment may be a computer in which a control unit 410, a communication circuit 420, an operation input unit 430, a storage unit 440, an output device 450, and a sensor unit 460 are electrically connected. Furthermore, in the electronic device 100, the antenna circuit 150 is electrically connected to the communication circuit 420, and a battery 470 supplies energy to each element in FIG. 4.

The control unit 410 includes a central processing unit (CPU), a random-access memory (RAM), a read only memory (ROM), and the like. The CPU deploys the program stored in the storage unit 440 in the RAM. The control unit 410 can execute various information processing by the CPU interpreting and executing the program.

For example, the control unit 410 receives the received data from the communication circuit 420 and conversely also sends the transmission data to the communication circuit 420. Also, the control unit 410 sends the output data to the output device 450 and instructs the sensor unit 460 to start/end the measurement. Furthermore, the control unit 410 receives the user's operation input from the operation input unit 430 and performs: an operation in response to this, such as a screen transition of the display 160, transmission and reception of data to and from the user device 310, control of the start/end of the measurement by the sensor unit 460, and the like.

The operation input unit 430 is hardware configured to receive an operation input by a user. The operation input unit 430 may include, for example, a button, a crown, and the like provided on a side surface of the case 110 of the electronic device 100; or a touch-screen.

The storage unit 440 is a so-called auxiliary storage device, and can be, for example, a semiconductor memory such as a built-in flash memory. The storage unit 440 stores programs executed by the control unit 410, data used by the control unit 410 (for example, various sensor data), and the like. The output device 450 may include a display 160 and may include other devices such as speakers that output sound, musical pieces, and the like.

The sensor unit 460 measures a predetermined physical quantity, generates sensor data, and sends the data to the control unit 410. In addition to a blood pressure monitor 461 illustrated in FIG. 4, the sensor unit 460 may include: a motion sensor (for example, an acceleration sensor, a gyro sensor, and the like); a camera (image sensor); a microphone; a pulse wave sensor; an environment sensor (for example, a temperature sensor, a humidity sensor, an atmospheric pressure sensor, and the like); and the like. Sensor data is not limited to raw sensing data and may also include data generated by correcting or processing.

The blood pressure monitor 461 can include a blood pressure monitor capable of continuously measuring the user's blood pressure every beat (hereinafter, referred to as a continuous blood pressure monitor). The continuous blood pressure monitor may continuously measure the user's blood pressure from the pulse transmit time (PTT), or the continuous measurement may be achieved by a tonometry method or another technique.

The blood pressure monitor 461 may also include, instead of or in addition to the continuous blood pressure monitor, a blood pressure monitor not capable of continuous measurement (hereinafter, referred to as a non-continuous blood pressure monitor). The non-continuous blood pressure monitor can be, for example, an oscillometric blood pressure monitor. An oscillometric blood pressure monitor detects the pressure pulse wave during the step of depressurizing the cuff after pressurization and determines the user's blood pressure based on this. In the case in which the blood pressure monitor 461 includes an oscillometric blood pressure monitor, the belt member 210 of the electronic device 100 may be used as a cuff, as previously described.

A non-continuous blood pressure sensor (in particular, an oscillometric blood pressure monitor) tends to have high measurement accuracy compared to a continuous blood pressure monitor. Thus, the blood pressure monitor, for example, may activate the non-continuous blood pressure monitor instead of the continuous blood pressure monitor when, as a trigger, a condition is satisfied (for example, the user's blood pressure data measured by the continuous blood pressure monitor displays a predetermined state) and measure the blood pressure data with higher accuracy.

Note that, with regard to a specific hardware configuration of the electronic device 100, components can be omitted, replaced, and added as appropriate according to the embodiment. For example, the control unit 410 may include a plurality of processors, and the electronic device 100 may be composed of a plurality of information processing devices, and the like.

Figure 5:
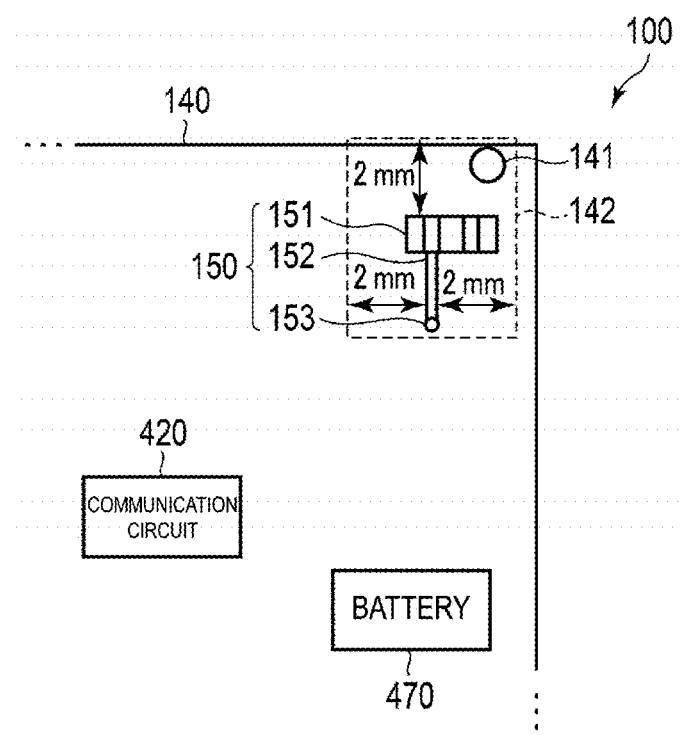
FIG. 5 is a diagram illustrating an example of the positional relationship between a hole portion, an antenna circuit, a communication circuit, and a battery installed on a substrate provided in an electronic device according to an embodiment.

The substrate 140 includes a plurality of hole portions passing through the front surface and the back surface of the substrate 140. One of these hole portions 141 is illustrated in FIG. 5. The substrate 140 may be fixed to a support body by being screwed together using the hole portion (141). Here, the support body may be the case 110 or may be another component such as, for example, a circuit case. Also, the threaded member for fixing the substrate 140 to the support body via the hole portion (141) may be metallic or include a metal material.

Metal bodies, such as the communication circuit 420 and the battery 470, affect the emission efficiency of the antenna circuit 150. A metal body at or near the location of an antinode of the antenna current induces a current in the opposite direction to the antenna current and reduces the apparent antenna current. This is thought to be one cause of reduction in the emission efficiency from the antenna circuit 150. The magnitude of the current induced by the metal body depends on the size of the metal body and the distance from the metal body to the antenna circuit 150. For this reason, the metal bodies are disposed outside of a prohibited region 142 of the substrate 140 defined around the antenna circuit 150.

Here, the prohibited region 142, for example, may be defined as an area within a predetermined distance value from the antenna circuit 150, that is, an antenna element 151, a feed element 152, and a feed point 153. However, the area from both end portions of the antenna circuit 150 onward, specifically, the area from the end of the antenna element 151 onward (the open end of the antenna element 151 and a position of a node of the antenna current) and the area from the feed point 153 onward (a position of an antinode of the antenna current) may be excluded from the prohibited region 142. Furthermore, in the case in which the parasitic capacitance that occurs between the end of the antenna element 151 and the case 110 of the electronic device 100 is used as a capacity hat connected to the antenna element 151, the area from the end of the antenna element 151 onward is included in the prohibited region 142. The predetermined value is, for example, 2 mm, but the predetermined value is not limited thereto. By providing the prohibited region 142 in this way, a reduction in emission efficiency, caused by a metal body being disposed near the antenna circuit 150, can be minimized or prevented.

Also, though the threaded member described above includes a metal material, it can be considered to be a floating conductor (also referred to as an insulated conductor) electrically isolated from the GND of the antenna circuit 150. Thus, the emission efficiency of the antenna circuit 150 is not greatly affected. Here, "floating conductor" can refer to a metal in a floating state or a metal that is electrically isolated from GND. Thus, by intentionally providing the hole portion 141 in the prohibited region 142, the prohibited region is prevented from being a completely dead space, and the limited space within the case of the electronic device 100 can be effectively utilized.

The antenna circuit 150 is installed on the substrate 140 and includes the antenna element 151, the feed element 152, and the feed point 153. The antenna element 151 is fed from the feed point 153 via the feed element 152. The feed point 153 is the connection point between the feed element 152 and the substrate 140.

Because the antenna element 151 installed inside the small electronic device 100, it preferably has a compact size. Thus, for example, the antenna element 151 may be a chip antenna provided with a ¼ wavelength antenna, such as a monopole antenna, an inverted L antenna, an inverted F antenna, and the like. However, the antenna element 151 is not limited to being a ¼ wavelength antenna and, instead of being a chip antenna, may be a printed circuit board (PCB) antenna, a flexible printed circuit (FPC) antenna, a cast metal antenna, or the like. In an example in which the antenna element 151 is a chip antenna, the antenna element 151, for example, includes: a conductor material, which forms an inductor, and a dielectric material and a magnetic material disposed in a layered manner.

The feed element 152 is connected between the antenna element 151 and the feed point 153. The feed element 152, for example, may be a wire, a pipe, or the like including a conductor material such as copper or may be formed by applying, etching, or printing a conductive foil on the substrate 140.

The communication circuit 420 is installed on the substrate 140 and is electrically connected to the antenna circuit 150. The communication circuit 420 performs at least one of a signal transmission process and a signal reception process via the antenna circuit 150. The communication circuit 420 may include, for example, a modulator, a digital-to-analog converter, an upconverter, a filter, a power amplifier, and the like for realizing signal transmission. Also, the communication circuit 420 may include, for example, a low-noise amplifier, a filter, a downconverter, an analog-to-digital converter, a demodulator, and the like for realizing signal reception. Furthermore, the communication circuit 420 may also include a switch for switching between transmission and reception of antenna circuit 150.

The battery 470 is installed on the substrate 140 and supplies energy to various elements in the electronic device 100 including the communication circuit 420. The battery 470, for example, may be a rechargeable battery such as a lithium ion battery, but may be another type of rechargeable battery, or a primary battery. Also, instead of the battery 470, an energy supply unit, which has a broader meaning, may be used. This energy supply unit may correspond to the battery 470 and may supply power generated by energy harvesting such as vibration power generation, for example.

Figure 6:
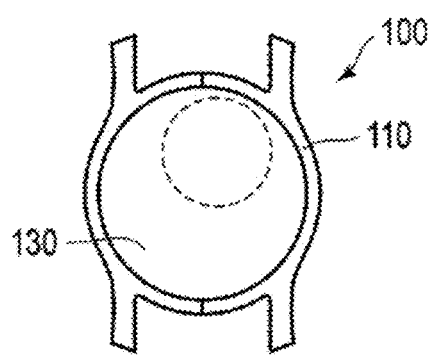
FIG. 6 is a bottom view illustrating an example of an electronic device according to an embodiment.

FIG. 6 illustrates an example of the back surface of the electronic device 100. Again, in the electronic device 100, the opening on the back surface of the case 110 is blocked by the back lid 130. Note that the case 110 and the back lid 130 need not necessarily be separate components and may be formed integrally.

Figure 7:
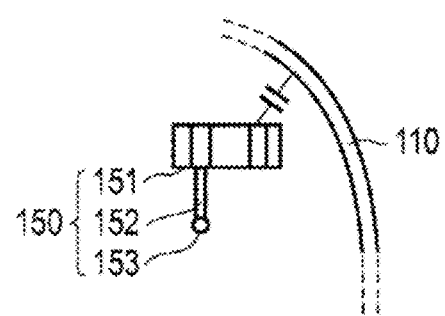
FIG. 7 is a explanatory diagram illustrating the relationship between an antenna circuit and a case in an electronic device according to an embodiment.

Furthermore, as described above, the case 110 has an effect of artificially extending the electrical length of the antenna circuit 150. In the region of the substrate 140 corresponding to the dashed line region of FIG. 6, as illustrated in FIG. 7, the end of the antenna element 151 is disposed in the proximity of a portion of the case 110, and parasitic capacitance occurs between the two. This parasitic capacitance may be considered a capacity hat and may equivalently extend the electrical length of antenna circuit 150 while minimizing or preventing a reduction in the emission efficiency of antenna circuit 150. The distance between the two are set to, for example, 2 mm or less, but is not limited thereto.

Figure 8:
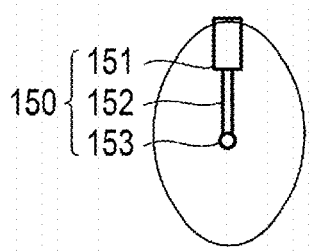
FIG. 8 is a diagram illustrating an example of the distribution of an antenna current in the case in which the antenna circuit operates alone.
Figure 9:
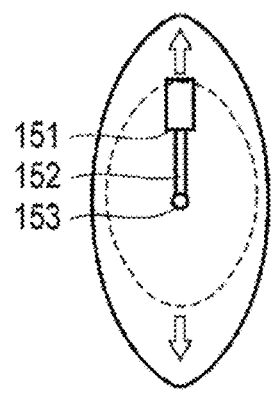
FIG. 9 is a diagram illustrating an example of the distribution of an antenna current in the case in which the antenna circuit is connected to a capacity hat.

When the antenna circuit 150 operates alone, as illustrated in FIG. 8, the antenna current is distributed such that the vicinity of the end (open end) of the antenna element 151 is a node and the vicinity of the feed point 153 is an antinode. On the other hand, when the capacity hat is connected to the antenna element 151, the position of the node of the antenna current extends further out from that illustrated in the example of FIG. 8. This is illustrated in FIG. 9. This is equivalent to extending the electrical length of the antenna circuit 150. Thus, even in the case in which the electrical length of the antenna circuit 150 is set shorter than the ¼ wavelength of the target frequency, the resonant frequency when the antenna circuit 150 operates can be brought close to the target frequency.

Actions and Effects

As described above, in the electronic device according to the embodiment, a glass lid that blocks the opening of the case surface is supported by the case with a gap formed therebetween, and the gap is filled with an insulating member. The insulating member seals the gap and increases waterproofing and dustproofing and forms an electrical slit, through which electromagnetic waves can pass, between the internal space and the external space of the case. Thus, with little limitation on the flexibility of the design of the electronic device, an emission port for electromagnetic waves transmitted and received by the antenna circuit can be secured.

3 Modified Example

While embodiments of the present invention have been described in detail above, the foregoing description is merely illustrative of the present invention in all respects. Of course, various modifications and variations can be made without departing from the scope of the present invention. For example, the following changes are possible. Note that, in the following, the same reference numerals are used for components similar to those of the above-described embodiment, and descriptions thereof will be omitted as appropriate. The following modified examples can be combined as appropriate.

4.1

Figure 10:
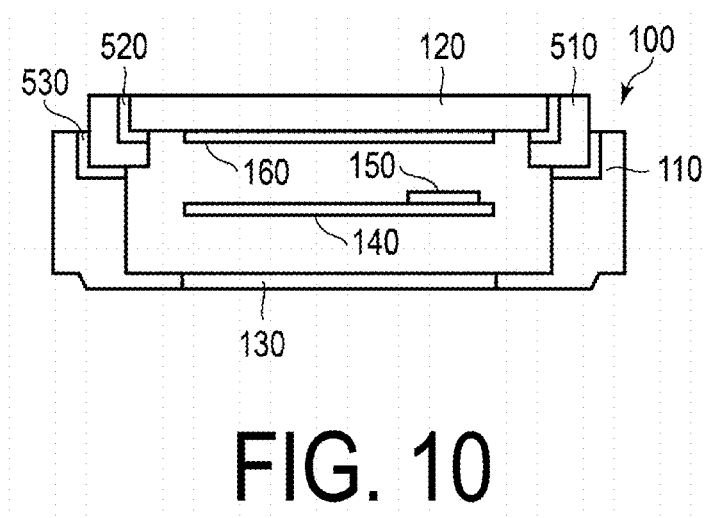
FIG. 10 is a cross-sectional view of a modified example of the example in FIG. 1.

Although FIG. 1 illustrates a cross-sectional structure of the electronic device 100, a modified example thereof is illustrated in FIG. 10. FIG. 10 illustrates another example of a cross-section of the electronic device 100 sectioned through the antenna circuit 150 in a plan view substantially perpendicular to the surface of the electronic device 100. Similar to the example illustrated in FIG. 1, the case 110 includes a projection portion that is provided on the inner wall surface connecting to the opening and that projects toward the opening inner side. However, rather than the projection portion supporting the glass lid 120, the projection portion supports an annular frame 510 with a gap formed therebetween.

The annular frame 510 is a substantially cylindrical frame body including an opening on the front surface and the back surface. The annular frame 510 includes a projection portion that is provided on the inner wall connecting to the opening that projects toward the opening inner side. The glass lid 120 is supported by the projection portion with a gap formed therebetween. The annular frame 510 serves as a cushioning when an external force is applied to the case 110 and is transmitted to the glass lid 120 or as decoration. Also, the annular frame 510 has an effect of increasing the number of electrical slits as described below. The annular frame 510 may also be referred to as a support member as it supports (indirectly) the glass lid 120.

An insulating member 520 fills the gap between the projection portion of the annular frame 510 and the glass lid 120. Also, an insulating member 530 fills the gap between the projection portion of the case 110 and the annular frame 510. The insulating member 520 and the insulating member 530 seal the gap and increase waterproofing and dustproofing and form electrical slits, through which electromagnetic waves can pass, between the internal space and the external space of the case 110. These electrical slits can be used as emission ports for electromagnetic waves transmitted and received by the antenna circuit 150. Note that a gap may be formed between the insulating member 520 and the insulating member 530 and the display 160 as illustrated in FIG. 10, or the insulating member 520 and the insulating member 530 may be in contact with the display 160.

The length of the emission port is preferably greater than or equal to the ¼ wavelength of the target frequency. In the case in which the glass lid has a disk shape with a diameter of approximately 3 cm, two emission ports the size of the outer circumference, i.e., approximately 10 cm, can be secured. This is a greater length than 3 cm, which is the length of the emission port required by electromagnetic waves in the 2.4 GHz band. These electrical slits are formed utilizing the gap between components of the electronic device 100 and does not require the case 110 or other components to be processed, for example, cut or the like. Thus, there is no limitation on the flexibility of the design of the electronic device 100.

Note that in the case in which one of the emission ports is unnecessary, the insulating member 520 or the insulating member 530 may be omitted. Also, the opening is not limited to the electrical slit formed between components described with reference FIGS. 1 and 10. In the case in which the electronic device 100 includes an opening for a different purpose such as non-contact power feeding, for example, the opening can be used as an emission port for electromagnetic waves transmitted and received by the antenna circuit 150. Furthermore, even in a case in which the size of the emission port is less than the ¼ wavelength of the target frequency, the reduction in the emission efficiency can be minimized or prevented by installing the antenna circuit 150 at or near the emission port.

However, the embodiments described above are merely illustrative of the invention in all respects. Of course, various modifications and variations can be made without departing from the scope of the present invention. In other words, specific configurations in accordance with an embodiment may be adopted as appropriate at the time of carrying out the present disclosure. Note that although data appearing in the present embodiment will be described using natural language, the data is more specifically designated by pseudo-language, commands, parameters, machine language, and the like that are recognizable by a computer.

A part or the entirety of the embodiment can be described, as described in the following supplementary notes in addition to the scope of the claims, but the present invention is not limited thereto.

1.
A wireless communication device (100), comprising:
a case (110) having a substantially cylindrical shape and including a first opening at a front surface and a second opening at a back surface, respectively;
a first cover member (120) that blocks at least a portion of the first opening;
a second cover member (130) that blocks at least a portion of the second opening;
an insulating member (170) that fills a gap between the first cover member and the case;
a display (160);
a substrate (140) housed by the case;
an antenna circuit (150) installed on the substrate; and
a communication circuit (420) installed on the substrate and electrically connected to the antenna circuit, wherein
the case includes a metal material; and
the first cover member includes a light-transmitting material that allows light from the display to pass through.

2.
A wireless communication device (100), comprising:
a case (110) having a substantially cylindrical shape and including a first opening at a front surface and a second opening at a back surface, respectively;
a first cover member (120) that blocks at least a portion of the first opening;
a support member (510) that supports the first cover member;
a second cover member (130) that blocks at least a portion of the second opening;
an insulating member (520) that fills a gap between the first cover member and the support member;
a display (160);
a substrate (140) housed by the case;
an antenna circuit (150) installed on the substrate;
a communication circuit (420) installed on the substrate and electrically connected to the antenna circuit, wherein
the case includes a metal material; and
the first cover member includes a light-transmitting material that allows light from the display to pass through.

3.
A wireless communication device (100), comprising:
a case (110) having a substantially cylindrical shape and including a first opening at a front surface and a second opening at a back surface, respectively;
a first cover member (120) that blocks at least a portion of the first opening;
a support member (510) that supports the first cover member;
a second cover member (130) that blocks at least a portion of the second opening;
an insulating member (530) that fills a gap between the support member and the case;
a display (160);
a substrate (140) housed by the case;
an antenna circuit (150) installed on the substrate;
a communication circuit (420) installed on the substrate and electrically connected to the antenna circuit, wherein
the case includes a metal material; and
the first cover member includes a light-transmitting material that allows light from the display to pass through.

REFERENCE SIGNS LIST

100 . . . Electronic device
110 . . . Case
120 . . . Glass lid
130 . . . Back lid
140 . . . Substrate
141 . . . Hole portion
142 . . . Prohibited region
150 . . . Antenna circuit
151 . . . Antenna element
152 . . . Feed element
153 . . . Feed point
160 . . . Display
170, 520, 530 . . . Insulating member
210 . . . Belt member
310 . . . User device
320 . . . Server
410 . . . Control unit
430 . . . Operation input unit
440 . . . Storage unit
450 . . . Output device
460 . . . Sensor unit
461 . . . Blood pressure monitor
420 . . . Communication circuit
470 . . . Battery
510 . . . Annular frame

The invention claimed is:

1. A wireless communication device comprising:
a case having a substantially cylindrical shape and including a first opening at a front surface and a second opening at a back surface, respectively;
a first cover member that blocks at least a portion of the first opening;
a support member that supports the first cover member;
a second cover member that blocks at least a portion of the second opening;
an insulating member that fills a gap between the first cover member and the support member;
a display;
a substrate housed by the case; and
an antenna circuit installed on the substrate;
a communication circuit installed on the substrate and electrically connected to the antenna circuit, wherein
the case includes a metal material,
the first cover member includes a light-transmitting material that allows light from the display to pass through,
the support member has a substantially cylindrical shape that includes a third opening at a front surface and a fourth opening at a back surface, respectively, and includes a projection portion projecting to an inner side of the third opening and the fourth opening and provided on an inner wall surface connecting to the third opening and the fourth opening, the first cover member is supported by the projection portion, and the insulating member fills a gap between the first cover member and each of the projection portion and the inner wall surface of the support member.

2. A wireless communication device comprising:

a case having a substantially cylindrical shape and including a first opening at a front surface and a second opening at a back surface, respectively;

a first cover member that blocks at least a portion of the first opening;

a support member that supports the first cover member;

a second cover member that blocks at least a portion of the second opening;

an insulating member that fills a gap between the support member and the case;

a display;

a substrate housed by the case;

an antenna circuit installed on the substrate; and a communication circuit installed on the substrate and electrically connected to the antenna circuit, wherein the case includes a metal material, the first cover member includes a light-transmitting material that allows light from the display to pass through, the support member has a substantially cylindrical shape that includes a third opening at a front surface and a fourth opening at a back surface, respectively, and includes a projection portion projecting to an inner side of the third opening and the fourth opening and provided on an inner wall surface connecting to the third opening and the fourth opening, the first cover member is supported by the projection portion of the support member, and the wireless communication device further comprises an insulating member that fills a gap between the first cover member and each of the projection portion and the inner wall surface of the support member.

3. The wireless communication device according to claim 2, wherein the case includes a projection portion projecting to an inner side of the first opening and the second opening and provided on an inner wall surface connecting to the first opening and the second opening, the support member is supported by the projection portion of the case, and the insulating member that fills the gap between the support member and the case is disposed to fill a gap between the support member and each of the projection portion and the inner wall surface of the case.

4. The wireless communication device according to claim 1, wherein the case includes a projection portion projecting to an inner side of the first opening and the second opening and provided on an inner wall surface connecting to the first opening and the second opening, and the wireless communication device further comprises an insulating member that fills a gap between the support member and each of the projection portion and the inner wall surface of the case.

5. The wireless communication device according to claim 1, wherein the second cover member does not include any metal material in at least one region of the second cover member, and a first orthographic projection of the at least one region of the second cover member projected on a plane substantially parallel with the substrate contains a second orthographic projection of an installed region of the antenna circuit projected on the plane identical.

6. A sensor device comprising:

the wireless communication device according to claim 1, and a sensor that measures a physical quantity and generates sensor data, wherein the communication circuit transmits the sensor data via the antenna circuit.

7. A sensor device comprising:

the wireless communication device according to claim 1; and a sensor that measures a physical quantity and generates sensor data, wherein the display displays the sensor data.

8. The sensor device according to claim 7, wherein the sensor includes a blood pressure monitor.

9. A wearable device comprising:

the sensor device according to claim 8; and a belt member connected to the case.

* * * * *